(12) United States Patent
Kim et al.

(10) Patent No.: US 9,816,021 B2
(45) Date of Patent: Nov. 14, 2017

(54) ANTIFREEZE MEMBER

(71) Applicants: SAMSUNG ELECTRONICS CO., LTD., Suwon-si, Gyeonggi-do (KR); Industry-University Cooperation Foundation Hanyang University (IUCF-HYU), Seoul (KR)

(72) Inventors: Hong Suk Kim, Seoul (KR); Myong Jong Kwon, Suwon-si (KR); Seung Jin Oh, Seoul (KR); Yunho Gwak, Seoul (KR); Young-Pil Kim, Seoul (KR); Ji-In Park, Seongnam-si (KR); EonSeon Jin, Seoul (KR)

(73) Assignees: SAMSUNG ELECTRONICS CO., LTD., Suwon-si (KR); INDUSTRY-UNIVERSITY COOPERATION FOUNDATION HANYANG UNIVERSITY (IUCF-HYU), Seoul (KR)

( * ) Notice: Subject to any disclaimer, the term of this patent is extended or adjusted under 35 U.S.C. 154(b) by 247 days.

(21) Appl. No.: 14/657,443

(22) Filed: Mar. 13, 2015

(65) Prior Publication Data
US 2015/0267100 A1   Sep. 24, 2015

(30) Foreign Application Priority Data
Mar. 18, 2014   (KR) .................. 10-2014-0031677

(51) Int. Cl.
| | | |
|---|---|---|
| *C09K 3/18* | (2006.01) |
| *C09D 189/00* | (2006.01) |
| *C07K 17/14* | (2006.01) |
| *C08H 1/00* | (2006.01) |
| *F28F 19/00* | (2006.01) |
| *F28F 19/04* | (2006.01) |

(52) U.S. Cl.
CPC ................ *C09K 3/18* (2013.01); *C07K 17/14* (2013.01); *C08H 1/00* (2013.01); *C09D 189/00* (2013.01); *F28F 19/006* (2013.01); *F28F 19/04* (2013.01); *Y10T 428/31678* (2015.04)

(58) Field of Classification Search
CPC .......... C09K 3/18; C09K 3/185; F28F 19/006; F28F 19/04
See application file for complete search history.

(56) References Cited

U.S. PATENT DOCUMENTS

2011/0039066 A1* 2/2011 Bauer .................... C07K 17/06
428/141

FOREIGN PATENT DOCUMENTS

EP   2 248 607 A1   11/2010
WO   2009/136186 A1   11/2009

OTHER PUBLICATIONS

Zuo, Aluminum- and mild steel-binding peptides from phase display, Appl Microbiol Biotechnol (2005) 68, pp. 505-509.*

(Continued)

*Primary Examiner* — Monique Jackson
(74) *Attorney, Agent, or Firm* — Staas & Halsey LLP

(57) ABSTRACT

An antifreeze member includes a metal substrate, and a first coating layer including a recombinant antifreeze protein in which a metal-binding protein is conjugated to a performance-enhancing reformed antifreeze protein, and being bonded to the metal substrate via the metal-binding protein.

15 Claims, 14 Drawing Sheets
(4 of 14 Drawing Sheet(s) Filed in Color)

(56) References Cited

OTHER PUBLICATIONS

Lins, Trehalose-Protein Interaction in Aqueous Solution, Proteins: Structure, Function, and Bioinformatics (2004) 55, pp. 177-186.*
Jain, Effect of trehalose on protein structure, Protein Science, published online 2008, vol. 18, pp. 24-36.*
Kaushik, Why Is Trehalose an Exceptional Protein Stabilizer?, The Journal of Biological Chemistry, (2003), vol. 278, No. 29, pp. 26458-26465.*
Boo, Thermal stress responses in Antarctic yeast, Glaciozyma antarctica PI12, characterized by real-time quantitative PCR, Polar Biol (2013) 36, pp. 381-389.*
Extended European Search Report dated Aug. 17, 2015 in corresponding European Patent Application No. 15153358.5.
Seker et al., "Material Binding Peptides for Nanotechnology", Molecules, vol. 16, No. 12, Feb. 9, 2011, pp. 1426-1451.
Gwak et al., "Antifreeze Protein in Antarctic Marine Diatom, *Chaetoceros neogracile*", Marine Biotechnology, vol. 12, No. 6, Dec. 22, 2009, pp. 630-639.
Ohtake et al., "Trehalose: Current Use and Future Applications", Journal of Pharmaceutical Sciences, vol. 100, No. 6, Feb. 18, 2011, pp. 2020-2053.
European Decision on Grant dated Sep. 23, 2016 in corresponding European Patent Application No. 15 153 358.5.

* cited by examiner

中略 …

ANTIFREEZE MEMBER

CROSS-REFERENCE TO RELATED APPLICATIONS

This application claims the benefit of Korean Patent Application No. 10-2014-0031677, filed on Mar. 18, 2014 in the Korean Intellectual Property Office, the disclosure of which is incorporated herein by reference.

BACKGROUND

1. Field

Embodiments of the present disclosure relate to an antifreeze member including an antifreeze protein.

2. Description of the Related Art

Although metal substrates have been widely used in the fields of semiconductors, energy, and bio sensors, frost or ice is often formed on the surfaces of the metal substrates under a very low temperature environment.

For example, aluminum substrates, widely used as cooling plates, have limited cooling efficiency since surface resistance is increased in a super-cooled state due to the formation of frost on the surfaces thereof and have reduced lifespans due to rapid corrosion thereby. Thus, there is a need to develop a technique to minimize and inhibit condensation on the metal substrate by treating the surface of the metal substrate with an antifreeze material capable of decreasing a freezing point of water.

Examples of antifreeze materials widely used to date include anti-freezing solutions (ethylene glycol), glycerols, and surfactants (alcohols, moisture removers, polysaccharides, and salts). However, since these materials generally induce concentration-dependent anti-freezing phenomena, they have been used as only additives in solutions. In addition, it is very difficult to accumulate these materials on the surface of a metal substrate in a regular form, and a surface-treatment is very complicated, thereby increasing manufacturing costs thereof.

Recently, antifreeze proteins (AFPs) capable of reducing a freezing point of water with a low concentration and found in various species living at low temperature have been reported. A major property of the antifreeze proteins is to decrease a freezing point of a solution by being directly adhered to ice and inhibiting the growth of ice crystals. This phenomenon is referred to as thermal hysteresis (TH).

It is known that these antifreeze proteins may be applied and utilized in a variety of fields including the medical field for storage of blood or eggs and the food industry for preservation of food. Therefore, applications and utilizations of antifreeze proteins will be described.

SUMMARY

Therefore, it is an aspect of the present disclosure to provide an antifreeze member surface-treated with a recombinant antifreeze protein in relation to application of the antifreeze protein in a variety of fields.

More particularly, an antifreeze member including a recombinant antifreeze protein in which a metal-binding protein is conjugated to an antifreeze protein derived from *Chaetoceros neogracile* that is an Antarctic marine diatom is provided.

It is another aspect of the present disclosure to provide an antifreeze member surface-treated with trehalose to improve stability of an antifreeze protein.

Additional aspects of the disclosure will be set forth in part in the description which follows and, in part, will be obvious from the description, or may be learned by practice of the disclosure.

In accordance with one aspect of the present disclosure, an antifreeze member includes a metal substrate, and a first coating layer including a recombinant antifreeze protein in which a metal-binding protein is conjugated to a performance-enhancing reformed antifreeze protein, and bonded to the metal substrate via the metal-binding protein.

The performance-enhancing reformed antifreeze protein may include a protein including a mutation at an amino acid level and/or nucleic acid level in an antifreeze protein derived from *Chaetoceros neogracile*, as an Antarctic marine diatom.

The mutation may include a substitution of glycine, which is 143rd amino acid of the *Chaetoceros neogracile*-derived antifreeze protein, with tyrosine and/or threonine.

The metal-binding protein may include an Al-binding peptide.

The metal substrate may include aluminum (Al).

The antifreeze member may further include a second coating layer fixed to the first coating layer and including trehalose.

In accordance with another aspect of the present disclosure, an antifreeze member includes a metal substrate, a first coating layer including a metal-binding protein and fixed to the metal substrate via the metal-binding protein, and a second coating layer including a performance-enhancing reformed antifreeze protein and fixed to the first coating layer.

One end of the metal-binding protein may include a first linker, one end of the performance-enhancing reformed antifreeze protein may include a second linker, and the second coating layer may be fixed to the first coating layer via a bonding between the first linker and the second linker.

The performance-enhancing reformed antifreeze protein may include a protein including a mutation at an amino acid level and/or nucleic acid level in an antifreeze protein derived from *Chaetoceros neogracile*, as an Antarctic marine diatom.

The mutation may include a substitution of glycine, which is 143rd amino acid of the *Chaetoceros neogracile*-derived antifreeze protein, with tyrosine and/or threonine.

The metal-binding protein may include an Al-binding peptide.

The metal substrate may include aluminum (Al).

The antifreeze member may further include a third coating layer fixed to the second coating layer and including trehalose.

BRIEF DESCRIPTION OF THE DRAWINGS

The patent or application file contains at least one drawing executed in color. Copies of this patent or patent application publication with color drawing(s) will be provided by the Office upon request and payment of the necessary file.

These and/or other aspects of the disclosure will become apparent and more readily appreciated from the following description of the embodiments, taken in conjunction with the accompanying drawings of which.

DETAILED DESCRIPTION

Figure 1:
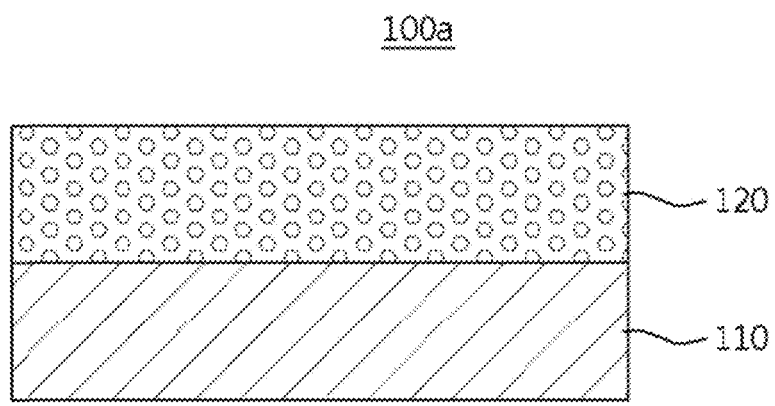
FIG. 1 is a diagram illustrating a structure of an antifreeze member according to an embodiment of the present disclosure.

Reference will now be made in detail to the embodiments of the present disclosure, examples of which are illustrated in the accompanying drawings, wherein like reference numerals refer to like elements throughout.

It will be understood that, although the terms "first", "second", etc., may be used herein to describe various elements, these elements should not be limited by these terms. The above terms are used only to distinguish one component from another. For example, a first component discussed below could be termed a second component, and similarly, a second component may be termed a first component without departing from the teachings of this disclosure. As used herein, the term "and/or" includes any and all combinations of one or more of the associated listed items.

As used herein, the term "polypeptide" refers to a polymer of two or more amino acids and may be used interchangeably with protein, and one of the two terms is used as a concept including both of them.

As used herein, the term "recombinant protein" refers to a protein expressed by a base sequence including a new combination of genotypes caused by crossing over of two different genetic materials.

As used herein, the term "recombinant antifreeze protein" is used to indicate a protein expressed by a base sequence in which a genetic material of a reformed antifreeze protein and a genetic material of a metal-binding peptide are combined.

In addition, the term "performance-enhancing reformed antifreeze protein" is used to indicate a protein that has undergone a mutation process at the amino acid and/or base sequence level to improve activity of an antifreeze protein derived from *Chaetoceros neoracile*, which is an Antarctic marine diatom extracted directly from nature.

The terms used in the present specification are merely used to describe particular embodiments, and are not intended to limit the present disclosure. An expression used in the singular encompasses the expression of the plural, unless it has a clearly different meaning in the context. In the present specification, it is to be understood that the terms such as "including" or "having," etc., are intended to indicate the existence of the features, numbers, steps, components, or combinations thereof disclosed in the specification, and are not intended to preclude the possibility that one or more other features, numbers, steps, components, or combinations thereof may exist or may be added.

Figure 2:
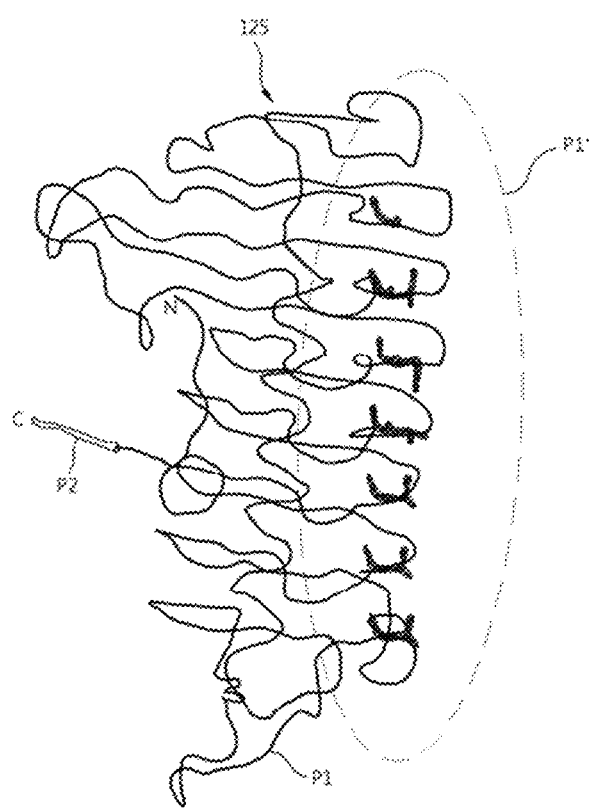
FIG. 2 is a diagram illustrating a structure of a recombinant antifreeze protein included in the antifreeze member.
Figure 3:
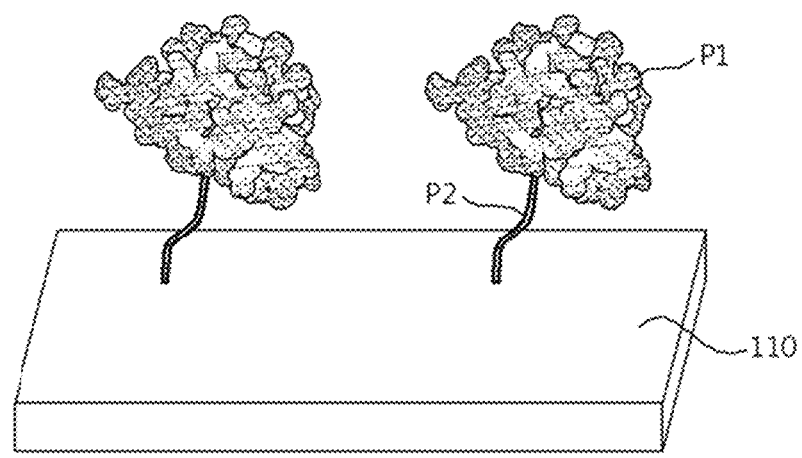
FIG. 3 is an enlarged diagram illustrating a binding structure of the antifreeze member of FIG. 1.

FIG. 1 is a diagram illustrating a structure of an antifreeze member 100a according to an embodiment of the present disclosure. FIG. 2 is a diagram illustrating a structure of a recombinant antifreeze protein 125 included in the antifreeze member 100a. FIG. 3 is an enlarged diagram illustrating a binding structure of the antifreeze member 100a of FIG. 1.

Referring to FIGS. 1 and 2, the antifreeze member 100a includes a metal substrate 110 and a first coating layer 120 including a recombinant antifreeze protein 125 in which a metal-binding protein P2 is conjugated to a performance-enhancing reformed antifreeze protein P1 and bonded to the metal substrate 110 via the metal-binding protein P2.

The metal substrate 110 to which the first coating layer 120 is fixed may include an aluminum (Al) component. In addition, the metal substrate 110 may be a pretreated metal substrate. If the metal substrate 110 is not pretreated, the first coating layer 120 or the like may not be fixed thereto due to weak adhesive force.

For example, since aluminum oxide ($Al_2O_3$) is formed on the surface of an aluminum (Al) substrate, the aluminum substrate has a structure to which the first coating layer 120 is not easily fixed. Thus, a pretreatment process is performed to form a plurality of hydroxyl (—OH) groups on the surface of the metal substrate 110, so that interactions between hydroxyl groups included in the recombinant antifreeze protein (AFT) 125 of the first coating layer 120 and hydroxyl groups of the surface of the metal substrate 110 vigorously occur. As a result, adhesive force of the first coating layer 120 to the metal substrate 110 may be improved.

The recombinant antifreeze protein 125 according to an exemplary embodiment may be a combination of a performance-enhancing reformed antifreeze protein derived from *Chaetoceros neogracile*, which is an Antarctic marine diatom," and a "metal-binding protein".

The performance-enhancing reformed antifreeze protein may be a mutated *Chaetoceros neogracile*-derived antifreeze protein obtained by substituting glycine, which is the 143rd amino acid, with tyrosine and/or threonine and may include fragments having various lengths and anti-freezing activity.

In addition, the performance-enhancing reformed antifreeze protein may further include an artificial mutation of a part of a sequence and/or a natural mutation. Such mutations may include not only mutations at the amino acid level, but also mutations at the nucleic acid level, and a mutation of nucleic acid may or may not involve a variation of amino acid corresponding thereto.

If a mutation involves a variation of amino acid, a gene causing the variation may encode a polypeptide having at least one substituted, deleted, added, and/or inserted amino acid. Such polypeptides may include mutants, derivatives, alleles, variants, and homologues.

Degeneracy mutation of a polynucleotide sequence may be an example of a mutation not involving a variation of amino acid, and degeneracy mutants may be included in a sequence of the illustrated embodiment of the present disclosure.

In addition, amino acid codon preference may vary according to types of hosts to express the recombinant antifreeze protein 125 in appropriate hosts, and the mutation of the performance-enhancing reformed antifreeze protein may include a mutation according to the amino acid codon preference.

Al-binding peptide is conjugated to one end of the performance-enhancing reformed antifreeze protein such that the recombinant antifreeze protein 125 is easily immobilized onto the metal substrate 110. This conjugated structure may be implemented through a genetic recombination process. That is, the conjugated structure may be obtained by joining a gene encoding the Al-binding peptide to one end of a gene encoding the performance-enhancing reformed antifreeze protein, and introducing the joined gene into a vector.

Hereinafter, a structure of the recombinant antifreeze protein 125 according to embodiments of the present disclosure will be described. FIG. 2 is a diagram illustrating a structure of the recombinant antifreeze protein 125.

As illustrated in FIG. 2, the recombinant antifreeze protein 125 may have a "performance-enhancing reformed antifreeze protein site P1" having anti-freezing activity and a "metal-binding protein site P2" bonding to the metal substrate 110.

The performance-enhancing reformed antifreeze protein site P1 may have a flat ice-binding site P1'. The ice-binding site P1' provides anti-freezing activity onto the surface of the first coating layer 120. The anti-freezing activity is activity inhibiting the growth of ice crystals. The flat ice-binding site P1' of the recombinant antifreeze protein 125 according to the illustrated embodiment is bonded to particular surfaces of very small ice crystals via hydrogen bonds or hydrophobic interactions, thereby inhibiting the growth of the ice crystals and re-crystallization of ice and reducing a freezing point of a solution to cause a difference between a melting point and the freezing point. This phenomenon is referred to as thermal hysteresis (TH). As thermal hysteresis is applied to the metal substrate 110, an anti-freezing structure delaying formation of ice on the surface thereof is provided.

The metal-binding protein site P2 is bonded to one end of the performance-enhancing reformed antifreeze protein P1 serving as a linker to immobilize the recombinant antifreeze protein 125 on the metal substrate 110. Since general antifreeze proteins do not include a linker serving as a medium immobilized onto the metal substrate 110, the antifreeze proteins cannot be easily attached to the metal substrate 110 alone. Accordingly, by providing the recombinant antifreeze protein 125 to which the metal-binding protein site P2 is conjugated, the recombinant antifreeze protein 125 may be immobilized onto the metal substrate 110 via the metal-binding protein site P2.

The metal-binding protein according to the illustrated embodiment may include the Al-binding peptide. However, the metal-binding protein is not limited thereto and should be understood to include various types of metal-binding proteins within the range of design modification which could be made by one of ordinary skill in the art.

Hereinafter, a binding structure of the antifreeze member 100a of FIG. 1 will be described in detail with reference to FIG. 3.

Referring to FIG. 3, the recombinant antifreeze protein 125 may be immobilized onto an aluminum (Al) substrate via the Al-binding peptide P2. That is, the Al-binding peptide P2 may function as a linker to immobilize the recombinant antifreeze protein 125 onto the Al substrate 110. Thus, the recombinant antifreeze protein 125 is immobilized onto the Al substrate 110 via the Al-binding peptide P2, thereby providing anti-freezing properties.

Figure 4:
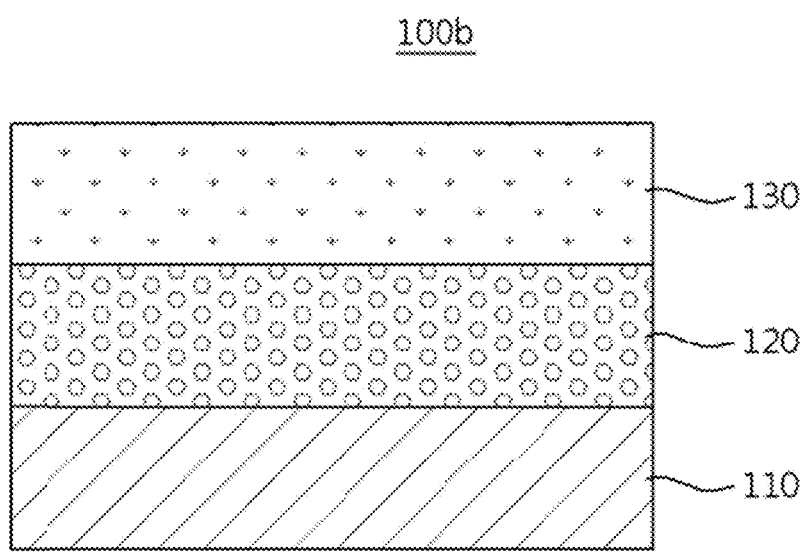
FIG. 4 is a diagram illustrating a structure of the antifreeze member further including a second coating layer.

An antifreeze member 100b according to another embodiment of the present disclosure may further include a second coating layer 130, as shown in FIG. 4.

Referring to FIG. 4, the antifreeze member 100b includes the same constituent elements as the antifreeze member 100a of FIG. 1, except that the antifreeze member 100b further includes the second coating layer 130. Since the constituent elements of FIG. 4 are substantially the same as those of FIG. 3 except for the second coating layer 130, descriptions thereof will not be repeated herein.

The second coating layer 130 is formed on the first coating layer 120. The second coating layer 130 may include trehalose such that anti-freezing properties provided to the metal substrate 100 by the first coating layer 120 are maintained.

Trehalose is a non-reducing disaccharide formed of two glucose units via (1→1) bond and having three kinds of isomers as represented by Structural Formula 1 below.

Structural Formula 1

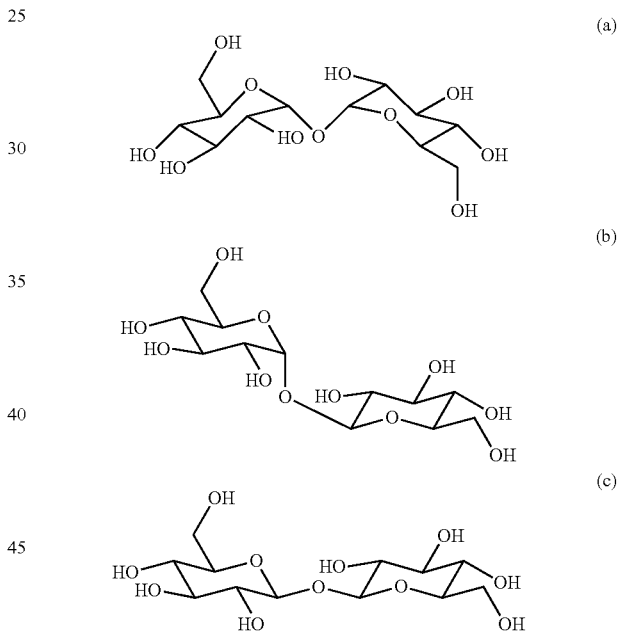

In Structural Formula 1, (a) is α,α-trehalose, (b) is α,β-trehalose, and (c) is β,β-trehalose.

The α,α-trehalose that is most widely distributed in nature is one of energy storage carbohydrates in bacteria, fungi, yeast, insects, animals, and plants, acts as a power source of insects for flying, and acts as a resistant material against external physical influence in yeast and *E. coli*.

Trehalose may be used not only as a sweetener, but also as a stabilizer of biomolecules with various applications in basic sciences, medical sciences, agricultural sciences, bioelectronics, and the like. Trehalose may be used as a stabilizer in dried or frozen food and as a diagnostic reagent and a pharmaceutical additive in drugs. Furthermore, trehalose may be used not only as a stabilizer to inhibit thermal coagulation and thermal denaturation of biologically active proteins including enzymes, but also a moisturizer in cosmetics.

Thus, the recombinant antifreeze protein may be protected by forming the second coating layer 130 including trehalose on the first coating layer 120.

The second coating layer 130 may have various shapes according to an amino acid sequence included in the recombinant antifreeze protein 125. For example, the second coating layer 130 may have a net-shaped structure to which a layer of water molecules is absorbed and may be formed on the first coating layer 120 including the recombinant antifreeze protein 125. The first coating layer 120 may be protected from external physical/chemical stimuli by the second coating layer 130. In addition, the recombinant antifreeze protein 125 may contact the surfaces of ice crystals through the net-shaped structure of the second coating layer 130, thereby inhibiting the growth of ice crystals.

Figure 5:
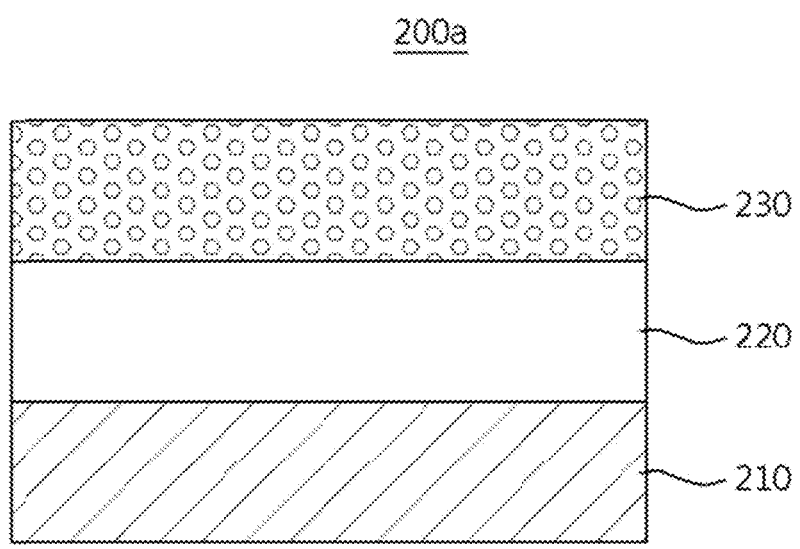
FIG. 5 is a diagram illustrating a structure of an antifreeze member according to another embodiment of the present disclosure.

Hereinafter, antifreeze members 200a and 200b according to other embodiments of the present disclosure will be described. FIG. 5 is a diagram illustrating a structure of an antifreeze member 200a according to another embodiment of the present disclosure.

Referring to FIG. 5, the antifreeze member 200a includes a metal substrate 210, a first coating layer 220, and a second coating layer 230.

The metal substrate 210 to which the first coating layer 220 is fixed may include an aluminum (Al) component. In addition, the metal substrate 210 may be a pretreated metal substrate. The metal substrate 210 according to the illustrated embodiment is substantially the same as the metal substrate 110 of FIG. 1, and thus descriptions thereof will not be repeated herein.

The first coating layer 220 may serve as a medium linking the second coating layer 230 with the metal substrate 210. More particularly, the first coating layer 220 may include a metal-binding protein and may easily be fixed to the metal substrate 210 via the metal-binding protein. The metal-binding protein may include an Al-binding peptide, and the first coating layer 220 may easily be fixed to an Al substrate including the Al component via the Al-binding peptide. In addition, the metal-binding protein may include a first linker (not shown) at the C-terminal thereof. The first linker (not shown) may be provided such that the second coating layer 230, which will be described later, is easily fixed to the first coating layer 220.

The second coating layer 230 may include the recombinant antifreeze protein 125 and may provide anti-freezing properties to the metal substrate 210. In addition, the recombinant antifreeze protein 125 may include a second linker (not shown) at the N-terminal thereof. The second linker (not shown) is linked to the first linker (not shown) bonded to one end of the metal-binding protein of the first coating layer 220, such that the second coating layer 230 is easily fixed to the first coating layer 220.

Figure 6:
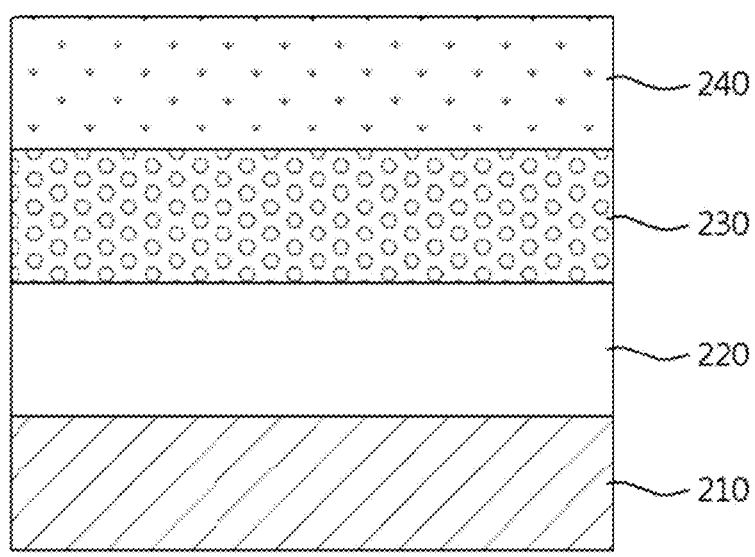
FIG. 6 is a diagram illustrating a structure of the antifreeze member further including a third coating layer.

The antifreeze member 200b may further include a third coating layer 240. FIG. 6 is a diagram illustrating a structure of the antifreeze member 200b further including the third coating layer 240.

Referring to FIG. 6, the antifreeze member 200b includes the same constituent elements as the antifreeze member 200a of FIG. 5, except that the antifreeze member 200b further includes the third coating layer 240. Since the constituent elements of FIG. 6 are substantially the same as those of FIG. 5 except for the third coating layer 240, descriptions thereof will not be repeated herein.

The third coating layer 240 is formed on the second coating layer 230. The third coating layer 240 may include trehalose such that anti-freezing properties provided to the metal substrate 210 by the second coating layer 230 are maintained. Trehalose enables stable immobilization of the performance enhancing reformed antifreeze protein included in the second coating layer 230, and the principle thereof is substantially the same as that of FIG. 4. Thus, descriptions thereof will not be repeated herein.

Hereinafter, one or more embodiments of the present disclosure will be described in greater detail with reference to the following experimental examples.

Experimental Example 1

As an experimental group, a recombinant antifreeze protein 125 in which an Al-binding peptide was conjugated to a performance-enhancing reformed antifreeze protein was coated on an Al substrate. As a control group, a performance-enhancing reformed antifreeze protein not including the Al-binding peptide was coated on an Al substrate. The coating was performed by dipping the Al substrate in a protein solution. After the protein coating process, the coating was identified by using an HRP-TMB method. The HRP-TMB method to detect histidine adhered to the recombinant antifreeze protein 125 may be used to identify whether the protein was coated on the Al substrate based on a phenomenon in which blue color is yielded in the presence of histidine.

Figure 7:
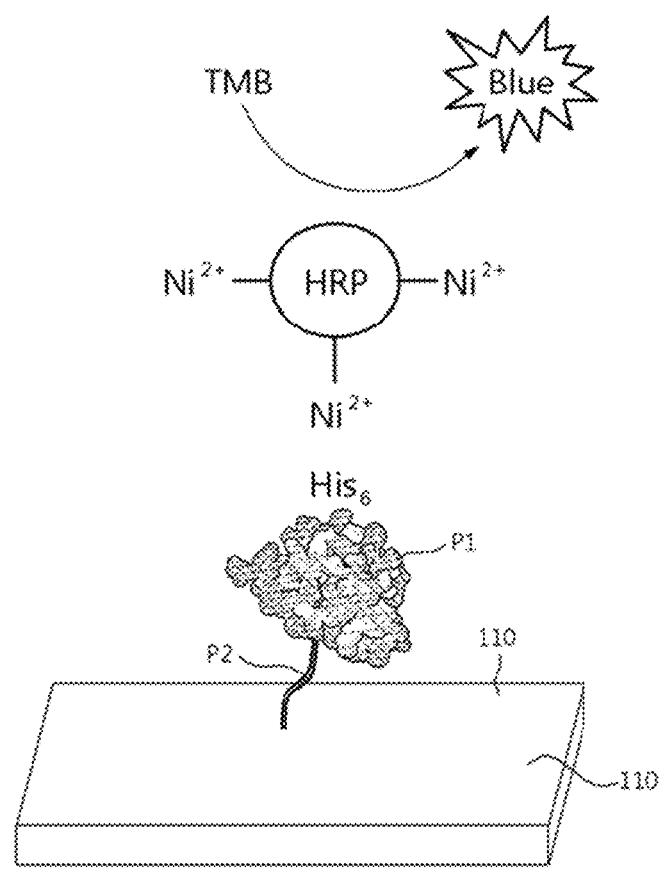
FIG. 7 is a diagram illustrating a principle of experiment according to Experimental Example 1.
Figure 8:
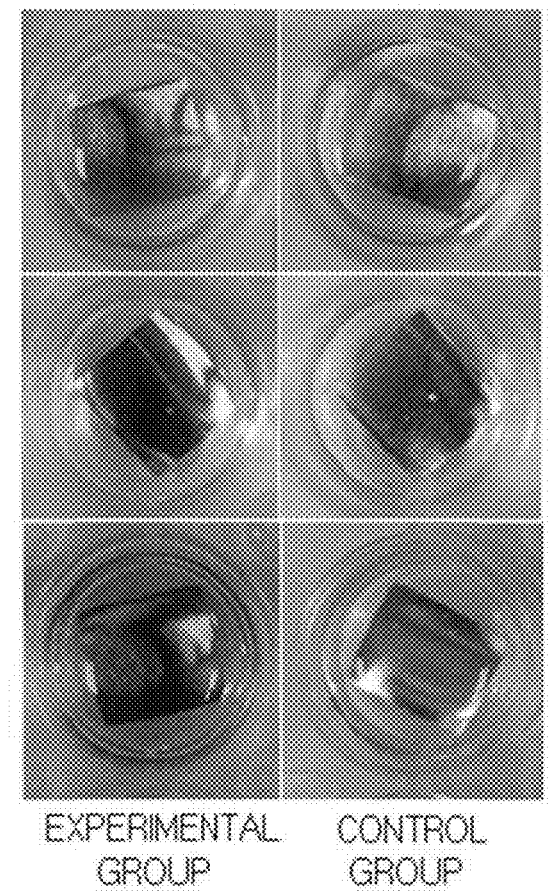
FIG. 8 is a diagram illustrating results of experiment according to Experimental Example 1.

FIG. 7 is a diagram illustrating a principle of experiment according to Experimental Example 1. FIG. 8 is a diagram illustrating results of experiment according to Experimental Example 1

As illustrated in FIG. 7, the recombinant antifreeze protein 125 includes histidine. Accordingly, when the HRP-TMB method is applied thereto after the protein coating process, horseradish peroxidase (HRP) is bonded near histidine due to interaction between a nickel cation of HRP and histidine, and a structure of 3,3'5,5'-tetramethylbenidine (TMB) is changed by the HRP, thereby yielding blue color.

As a result of the experiment, when the recombinant antifreeze protein 125 in which the Al-binding peptide was conjugated to the performance-enhancing reformed antifreeze protein was coated on the Al substrate, the structure of TMB was changed by the HRP, and blue color was yielded. On the contrary, when the performance-enhancing reformed antifreeze protein not including the Al-binding peptide was coated on the Al substrate in the control group, blue color was not yielded. That is, it was confirmed that the performance-enhancing reformed antifreeze protein was stably immobilized onto the Al substrate by the Al-binding peptide.

Experimental Example 2

As an experimental group, a metal substrate 110, which was coated with the recombinant antifreeze protein 125 in which the Al-binding peptide was conjugated to the performance-enhancing reformed antifreeze protein, was immersed in 1 ml of a phosphate buffered saline ("PBS") solution including 0.1% trehalose for 1 hour was prepared in order to improve stability of the metal substrate 110. Then, the metal substrate 110 was washed using the PBS solution and maintained at room temperature. As a control group, a metal substrate 110 not coated with trehalose was prepared. Then, the HRP-TMB method as illustrated in FIG. 7 was used to identify the degree of denaturation of the recombinant antifreeze proteins 125 of the experimental group and the control group.

Figure 9:
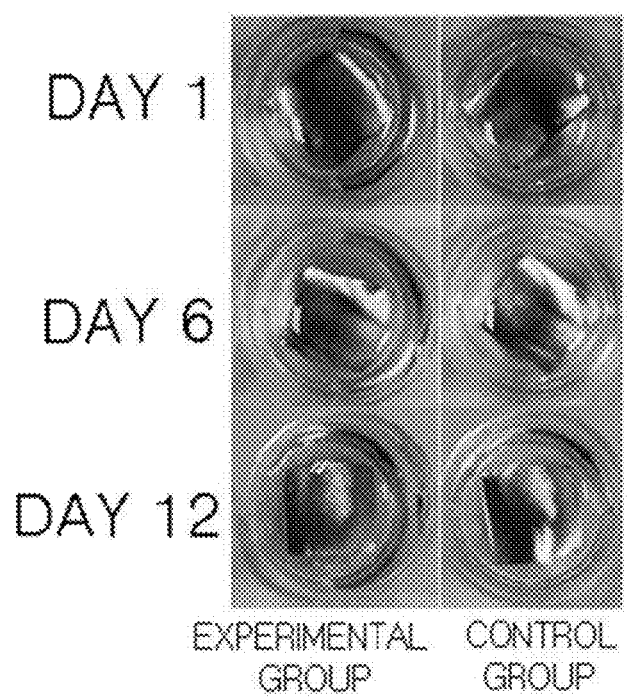
FIG. 9 is a diagram illustrating comparison results between stability of an immobilized structure of a recombinant antifreeze protein coated with trehalose and stability of an immobilized structure of a recombinant antifreeze protein not coated with trehalose.

The results are illustrated in FIG. 9. Referring to FIG. 9, when trehalose was coated on the metal substrate 110, blue color was exhibited after 12 days. That is, it was confirmed that the recombinant antifreeze protein 125 was stably immobilized onto the metal substrate 110 by the trehalose coating. However, when trehalose was not coated on the metal substrate 110, blue color was exhibited after 6 days but was not exhibited after 12 days. That is, it was confirmed that the recombinant antifreeze protein 125 was not stably immobilized onto the metal substrate 110 not coated with trehalose, and the surface thereof was denatured.

Experimental Example 3

Ultra-low temperatures of the recombinant antifreeze protein 125, the antifreeze member 100a onto which the recombinant antifreeze protein 125 is immobilized, and the antifreeze member 100b further including a trehalose coating layer were measured. A differential scanning calorimetry was used to measure each of the ultra-low temperatures.

Figure 10:
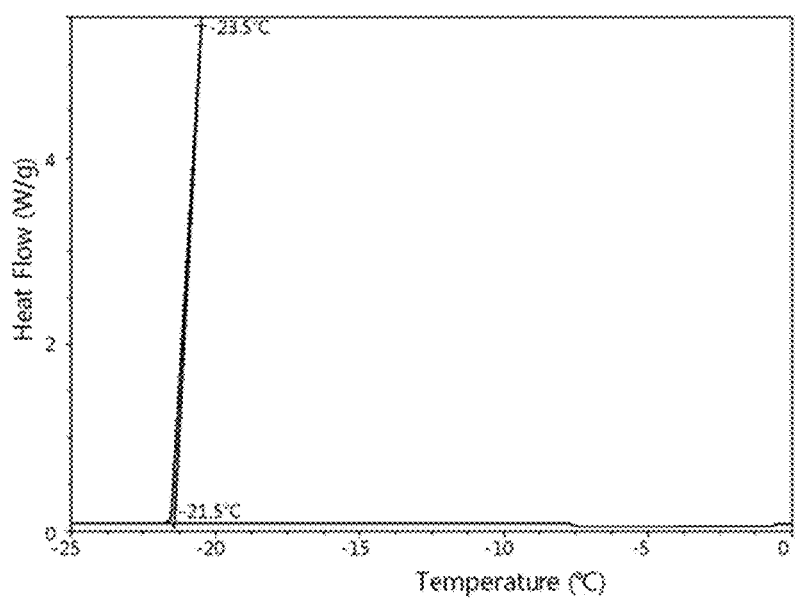
FIGS. 10, 11, and 12 are graphs respectively illustrating ultra-low temperatures of a recombinant antifreeze protein, a metal substrate onto which the recombinant antifreeze protein is immobilized, and the metal substrate further including a trehalose coating layer.
Figure 11:
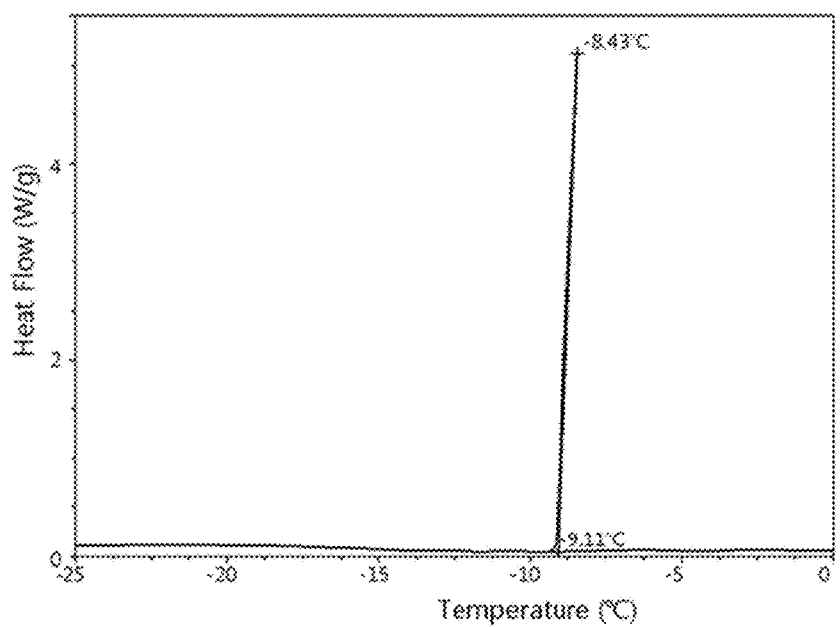
Figure 12:
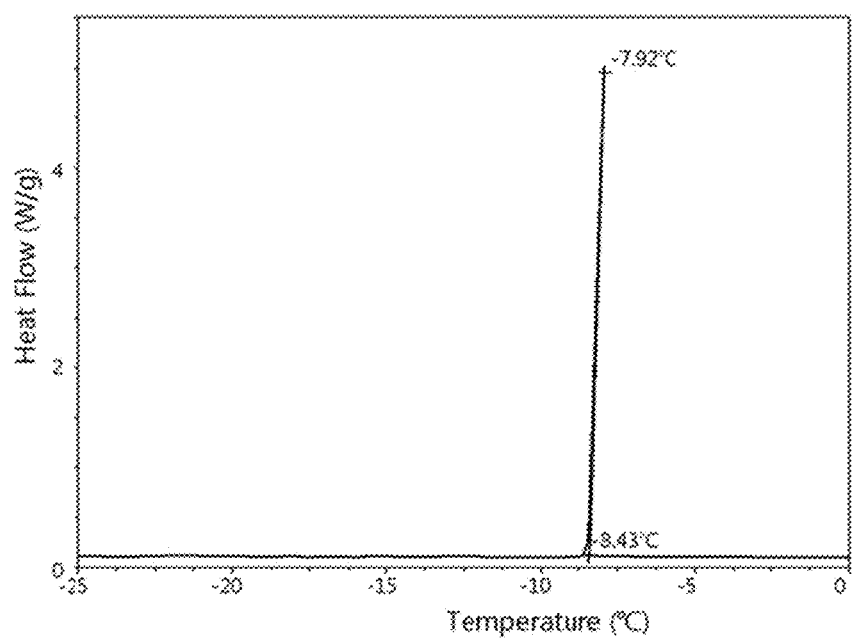

The results are shown in FIGS. 10, 11, and 12. FIG. 10 is a graph illustrating ultra-low temperature of the recombinant antifreeze protein 125. FIG. 11 is a graph illustrating ultra-low temperature of the antifreeze member 100a onto which the recombinant antifreeze protein 125 is immobilized. FIG. 12 is a graph illustrating ultra-low temperature of the antifreeze member 100b further including the trehalose coating layer.

Referring to FIG. 10, the ultra-low temperature of the recombinant antifreeze protein 125 was about −21.5° C. Referring to FIG. 11, the ultra-low temperature of the antifreeze member 100a onto which the recombinant antifreeze protein 125 was immobilized was about −9° C. Referring to FIG. 12, the ultra-low temperature of the antifreeze member 100b further including the trehalose coating layer was about −8° C. As a result of the experiment, the ultra-low temperature was the lowest when the recombinant antifreeze protein 125 was not immobilized onto the metal substrate 110. When the recombinant antifreeze protein 125 was immobilized onto the metal substrate 110, the ultra-low temperature was increased but still low. In addition, when the antifreeze protein was immobilized onto the metal substrate 110, the ultra-low temperature of the antifreeze member 100b further including the trehalose coating layer was relatively higher than that of the antifreeze member 100a not including the trehalose coating layer, but still low.

Experimental Example 4

Then, ice formation formed on the recombinant antifreeze protein 125 and the antifreeze member 100b coated with trehalose was measured while maintaining temperature of the metal substrate 110 at −3.5° C. by blowing air at a rate of 0.5 m/s at a relative humidity of 84% at a flow rate of 2 LPM for 3.5 hours. In addition, as control groups, ice formation on non-coated aluminum and hydrophilically coated aluminum was measured.

Figure 13A:
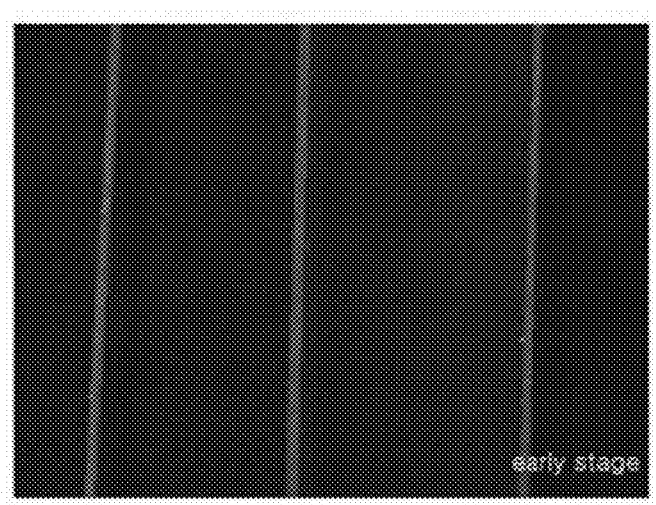
FIGS. 13A and 13B are diagrams respectively illustrating whether frost forms over time on non-coated aluminum, hydrophilically coated aluminum, and an antifreeze member according to the present invention.
Figure 13B:
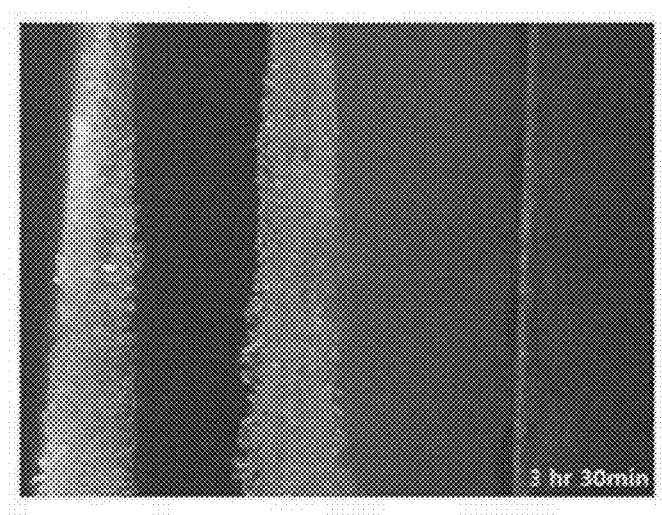

FIGS. 13A and 13B are diagrams illustrating results of the experiment. As illustrated in FIG. 13A, at an early stage, ice was not formed on each of the surfaces of the non-coated aluminum (left), hydrophilically coated aluminum (middle), and the antifreeze member 100b (right). However, as illustrated in FIG. 13B, after 3.5 hours, ice was formed on the surfaces of the non-coated aluminum (left) and hydrophilically coated aluminum (middle), but ice was not formed on the surface of the antifreeze member 100b (right).

In conclusion, in the antifreeze members 100a, 100b, 200a, and 200b according to the embodiments of the present disclosure, the recombinant antifreeze protein 125 may be stably bonded to the Al substrate via the Al-binding peptide site. In addition, since the coating layer including trehalose was formed on the surfaces of the antifreeze members 100a and 200a, anti-freezing properties of the recombinant antifreeze protein 125 may be stably maintained. Although the ultra-low temperature of the recombinant antifreeze protein 125 may be slightly increased due to the trehalose coating, the recombinant antifreeze protein 125 still has a low ultra-low temperature, and thus the anti-freezing properties of the recombinant antifreeze protein 125 may be stably expressed.

As is apparent from the above description, the antifreeze member according to the embodiments of the present disclosure provides the following effects.

First, the antifreeze protein is adhered to the surface of the metal substrate, and thus freezing of the metal substrate may be prevented.

In addition, if the antifreeze protein is utilized in a heat exchanger, not only a continuous cooling at high temperature, but also a continuous heating at low temperature may be achieved.

Although a few embodiments of the present disclosure have been shown and described, it would be appreciated by those skilled in the art that changes may be made in these embodiments without departing from the principles and spirit of the invention, the scope of which is defined in the claims and their equivalents.

What is claimed is:

1. An antifreeze member comprising:
   a metal substrate; and
   a first coating layer comprising a recombinant antifreeze protein in which a metal-binding protein is conjugated to a performance-enhancing reformed antifreeze protein, and bonded to the metal substrate via the metal-binding protein,
   wherein the performance-enhancing reformed antifreeze protein comprises a mutated protein comprising a mutation at an amino acid level and/or nucleic acid level, the mutated protein being derived from *Chaetoceros neogracile*, as an Antarctic marine diatom, and
   wherein the mutation comprises a replacement of glycine with tyrosine and/or threonine.

2. The antifreeze member according to claim 1, wherein the metal-binding protein comprises an aluminum-binding peptide.

3. The antifreeze member according to claim 1, wherein the metal substrate comprises aluminum.

4. The antifreeze member according to claim 1, further comprising a second coating layer fixed to the first coating layer and comprising trehalose.

5. The antifreeze member according to claim 1, wherein the metal substrate further comprises a pretreated surface.

6. The antifreeze member according to claim 1, wherein the recombinant antifreeze protein includes an ice binding site.

7. A heat exchanger including the antifreeze member according to claim 1.

8. An antifreeze member comprising:
   a metal substrate;
   a first coating layer comprising a metal-binding protein and being fixed to the metal substrate via the metal-binding protein; and a second coating layer comprising a performance-enhancing reformed antifreeze protein and being fixed to the first coating layer, wherein the performance-enhancing reformed antifreeze protein comprises a mutated protein comprising a mutation at an amino acid level and/or nucleic acid level, the mutated protein being derived from *Chaetoceros neogracile*, as an Antarctic marine diatom, and wherein the mutation comprises a replacement of glycine, with tyrosine and/or threonine.

9. The antifreeze member according to claim 8, wherein one end of the metal-binding protein comprises a first linker, one end of the performance-enhancing reformed antifreeze protein comprises a second linker, and the second coating layer is fixed to the first coating layer via a bond between the first linker and the second linker.

10. The antifreeze member according to claim 8, wherein the metal-binding protein comprises an aluminum-binding peptide.

11. The antifreeze member according to claim 8, wherein the metal substrate comprises aluminum.

12. The antifreeze member according to claim 8, further comprising a third coating layer fixed to the second coating layer and comprising trehalose.

13. The antifreeze member according to claim 8, wherein the metal substrate further comprises a pretreated surface.

14. The antifreeze member according to claim 8, wherein the recombinant antifreeze protein includes an ice binding site.

15. The antifreeze member according to claim 8, wherein the second coating layer includes trehalose.

\* \* \* \* \*